United States Patent
Knauf et al.

(10) Patent No.: US 10,947,187 B2
(45) Date of Patent: Mar. 16, 2021

(54) METHOD FOR PRODUCING METHYLENE-DIPHENYLENE-DIISOCYANATES AND POLYMETHYLENE-POLYPHENYLENE-POLYISOCYANATES

(71) Applicant: Covestro Intellectual Property GmbH & Co. KG, Leverkusen (DE)

(72) Inventors: Thomas Knauf, Dormagen (DE); Peter Plathen, Krefeld (DE); Dirk Manzel, Moers (DE); Stefan Wershofen, Mönchengladbach (DE)

(73) Assignee: Covestro Intellectual Property GmbH & Co. KG, Leverkusen (DE)

( * ) Notice: Subject to any disclaimer, the term of this patent is extended or adjusted under 35 U.S.C. 154(b) by 0 days.

(21) Appl. No.: 16/957,188

(22) PCT Filed: Jan. 2, 2019

(86) PCT No.: PCT/EP2019/050026
§ 371 (c)(1),
(2) Date: Jun. 23, 2020

(87) PCT Pub. No.: WO2019/134909
PCT Pub. Date: Jul. 11, 2019

(65) Prior Publication Data
US 2020/0331848 A1    Oct. 22, 2020

(30) Foreign Application Priority Data
Jan. 5, 2018  (EP) ..................... 18150434

(51) Int. Cl.
C07C 263/20 (2006.01)
C07C 263/10 (2006.01)
C08G 18/02 (2006.01)
C08G 18/76 (2006.01)
C07C 265/14 (2006.01)

(52) U.S. Cl.
CPC .......... *C07C 263/20* (2013.01); *C07C 263/10* (2013.01); *C08G 18/022* (2013.01); *C08G 18/7664* (2013.01); *C07C 265/14* (2013.01)

(58) Field of Classification Search
CPC ... C07C 265/14; C07C 263/10; C07C 263/20; C08G 18/022; C08G 18/7664
See application file for complete search history.

(56) References Cited

U.S. PATENT DOCUMENTS

| | | | |
|---|---|---|---|
| 4,414,074 A | 11/1983 | Ellendt et al. | |
| 4,851,570 A | 7/1989 | Zaby et al. | |
| 5,599,968 A | 2/1997 | Bankwitz et al. | |
| 2005/0222291 A1* | 10/2005 | Pirkl | C08G 18/12 521/159 |
| 2006/0025556 A1 | 2/2006 | Koch et al. | |
| 2006/0173206 A1 | 8/2006 | Schal et al. | |
| 2007/0117997 A1 | 5/2007 | Keggenhoff et al. | |
| 2007/0265465 A1 | 11/2007 | Keggenhoff et al. | |
| 2007/0299279 A1 | 12/2007 | Pohl et al. | |
| 2009/0166180 A1 | 7/2009 | Bulan et al. | |
| 2009/0175121 A1 | 7/2009 | Rausch et al. | |
| 2009/0209784 A1 | 8/2009 | Lorenz et al. | |
| 2010/0298596 A1 | 11/2010 | Keggenhoff et al. | |
| 2011/0224456 A1 | 9/2011 | Koole et al. | |
| 2014/0264163 A1 | 9/2014 | Merenov et al. | |

FOREIGN PATENT DOCUMENTS

WO    2010095927 A1    8/2010
WO    2017050776 A1    3/2017

OTHER PUBLICATIONS

Siefken, W., Liebigs Ann. 562, 75-106 (1949).
Ullmanns Encyklopädie der technischen Chemie [Ullmann's Encyclopedia of Industrial Chemistry], 4th ed. (1977), vol. 13, p. 351 to 353.
Wegener, G. et. al., Applied Catalysis A: General 221 (2001), 303-335, Elsevier Science B.V.
Stepanski, M. et al., Combining Distillation and Crystallization, Sulzer Technical Review Apr. 2002, 40373-75.
International Search Report, PCT/EP2019/050026, dated Mar. 21, 2019, Authorized officer: Claude Ginoix.

* cited by examiner

*Primary Examiner* — Jafar F Parsa
*Assistant Examiner* — Blaine G Doletski
(74) *Attorney, Agent, or Firm* — Donald R. Palladino

(57) ABSTRACT

The invention relates to a method for producing methylene-diphenylene-diisocyanate and optionally a mixture of methylene-diphenylene-diisocyanate and polymethylene-polyphenylene-polyisocyanate, wherein, in a step α), a fraction (142) containing a methylene-diphenylene-diisocyanate and secondary components is provided, optionally via a step α.1), the separating of methylene-diphenylene-diisocyanate and secondary components from a fraction (100) containing methylene-diphenylene-diisocyanate and polymethylene-polyphenylene-polyisocyanate, and wherein, in a step β), the fraction (142) containing methylene-diphenylene-diisocyanate and secondary components is subjected to a purification comprising an isomer separation by distillation and/or crystallization in two or more sub-steps (a, b, ... ), obtaining two or more methylene-diphenylene-diisocyanate-reinfractions (140-1, 140-2, ... ) and a secondary component fraction (150), wherein the secondary component fraction (150) obtained in step β) is returned to one of the sub-steps of step β), wherein none of the methylene-diphenylene-diisocyanate-reinfractions (140-1, 140-2, ... ) from step β) are obtained as distillation or crystallization, and/or to step α.1), insofar as carried out.

14 Claims, 4 Drawing Sheets

METHOD FOR PRODUCING METHYLENE-DIPHENYLENE-DIISOCYANATES AND POLYMETHYLENE-POLYPHENYLENE-POLYISOCYANATES

CROSS-REFERENCE TO RELATED APPLICATIONS

This application is a national stage application under 35 U.S.C. § 371 of PCT/EP2019/050026, filed Jan. 2, 2019, which claims the benefit of European Application No. 18150434.1, filed Jan. 5, 2018, each of which is incorporated herein by reference.

The present invention relates to a process for preparing methylene diphenylene diisocyanate and optionally a mixture of methylene diphenylene diisocyanate and polymethylene polyphenylene polyisocyanate, in which, in a step α), a fraction comprising methylene diphenylene diisocyanate and secondary components is provided, optionally by a step α.1), the separation of methylene diphenylene diisocyanate and secondary components from a fraction comprising methylene diphenylene diisocyanate and polymethylene polyphenylene polyisocyanate, and in which, in a step β), the fraction comprising methylene diphenylene diisocyanate and secondary components is subjected to a purification comprising an isomer separation by distillation and/or crystallization in two or more partial steps to obtain two or more pure methylene diphenylene diisocyanate fractions and a secondary component fraction, wherein the secondary component fraction obtained in step β) is returned to one of the partial steps of step β) in which none of the pure methylene diphenylene diisocyanate fractions from step β) is obtained in the form of distillate or crystallizate, and/or, if conducted, to step α.1).

BACKGROUND

Isocyanates (1) are prepared in large volumes and serve mainly as starting materials for production of polyurethanes. They are usually prepared by reacting the corresponding amines (2) with phosgene (3), using phosgene in a stoichiometric excess. The reaction of the amines with the phosgene can be effected either in the gas phase or in the liquid phase, wherein the reaction can be conducted batchwise or continuously (W. Siefken, Liebigs Ann. 562, 75-106 (1949)). Processes for preparing organic isocyanates from primary amines and phosgene have already been described many times before; merely by way of example, reference is made to Ullmanns Encyklopadie der technischen Chemie [Ullmann's Encyclopedia of Industrial Chemistry], 4th ed. (1977), volume 13, p. 351 to 353 and G. Wegener et. al., Applied Catalysis A: General 221 (2001), 303-335, Elsevier Science B.V. Of interest on the industrial scale are both aromatic isocyanates, such as for example methylene diphenylene diisocyanate (MMDI henceforth—"monomeric MDI"), mixtures of MMDI and polymethylene polyphenylene polyisocyanates (i.e. the higher homologs of MMDI, PMDI henceforth, "polymeric MDI"; mixtures of MMDI and PMDI are referred to collectively as MDI henceforth) or toluylene diisocyanate (TDI), and aliphatic isocyanates, for example pentane 1,5-diisocyanate (PDI), hexamethylene 1,6-diisocyanate (HDI) or isophorone diisocyanate (IPDI). In addition, isocyanates having benzylic isocyanate groups are also important; particular mention should be made here of xylylene diisocyanate (XDI).

The modern industrial scale preparation of isocyanates is effected semicontinuously (batchwise performance of some of the preparation steps, for example batchwise reaction and continuous workup) or continuously (all steps continuous).

It is a feature of the process regime in the liquid phase, typically referred to as liquid phase phosgenation, that the reaction conditions are chosen such that at least the amine, crude isocyanate and phosgene reaction components, but preferably all the reactants, products and reaction intermediates, are in liquid form in a suitable solvent under the conditions chosen. On completion of conversion, a gas phase comprising the hydrogen chloride coproduct and unconverted phosgene (because it was used in a superstoichiometric amount) is separated; this leaves the desired isocyanate together with the solvent very substantially in the liquid phase. The crude isocyanate is thus obtained in the mixture with solvent as a liquid stream which is worked up to obtain pure isocyanate (and to recover solvent and dissolved fractions of phosgene and hydrogen chloride).

Accordingly, in all isocyanate preparation processes of relevance on the industrial scale, what is obtained is a liquid crude isocyanate stream which has to be worked up to obtain the desired isocyanate in pure form and to recover other valuable components such as solvent. This workup generally comprises the removal of solvent, dissolved phosgene and dissolved hydrogen chloride. This is followed by a fine purification of the isocyanate which, if required, may also comprise an isomer separation. Depending on the type of isocyanate, it is possible to conduct a separation of homologues prior to the fine purification. Particular mention should be made here of the partial separation of MMDI from the isocyanate mixture comprising MMDI and PMDI that has been very substantially freed of solvent, phosgene and hydrogen chloride to obtain an MMDI fraction containing insignificant traces at most of PMDI (crude MMDI), and a mixture of PMDI and MMDI.

The workup of a crude isocyanate stream on the industrial scale is not trivial because many different demands have to be taken into account at the same time. As well as the obtaining of the target product in a form of maximum purity, mention should be made here of the recovery of phosgene, hydrogen chloride and solvent with minimum loss, especially for the purpose of recycling thereof (optionally after further conversion, for instance of hydrogen chloride to chlorine) into the process. All this has to be effected under conditions of maximum economic viability, i.e. with minimum energy consumption and minimum loss of product of value (especially of isocyanate, which can enter into unwanted further reactions in the case of non-optimized workup).

There have already been many descriptions of the workup of a crude isocyanate, especially of crude MDI and specifically of crude MMDI, by distillation.

DE 3145010 A1 is concerned with a process for preparing 4,4'-MMDI of high purity by distillative separation of 4,4'-MMDI isomers from MDI obtained by phosgenation of aniline/formaldehyde condensates in a distillation stage (1), further distillation of the top product obtained here in a distillation stage (2) with removal of 0.5% to 20% by weight of the amount of product introduced into stage (2) as bottoms from stage (2), subsequent separation of 2,2'- and 2,4'-MMDI from the fraction obtained as top product from stage (2) in a downstream distillation stage (3), and distillative workup of the bottom product obtained in stage (3) to obtain high-purity 4,4'-MMDI. The temperatures of the condenser outlets from the distillation stage (1), (2) and (3) are adjusted here to 130° C. to 230° C. in such a way that the temperatures are 10° C. to 100° C. below the vapor temperature defined by the vacuum in each case. Moreover, the workup of the bottoms obtained in stage (3) is conducted in two stages in such a way that, in a first final stage (4), 50% by weight to 90% by weight of the bottoms from stage (3) is isolated in the form of pure 4,4'-MMDI as top product, and the bottoms from the first final stage (4) are separated in a second final stage (4') into a further fraction of pure 4,4'-MMDI as top product and a distillation residue as bottoms.

EP 1 561 746 A2 describes a process for preparing a fraction of diisocyanates of the diphenylmethane series, comprising at least 99% by weight of bicyclic methylene diphenyl diisocyanate based on the mass of the fraction, in which a) aniline and formaldehyde are converted in the presence of an acidic catalyst to di- and polyamines of the diphenylmethane series, comprising bicyclic methylenediphenyldiamine, and b) the di- and polyamines of the diphenylmethane series comprising bicyclic methylenediphenyldiamine are phosgenated, optionally in the presence of a solvent, to obtain a crude di- and polyisocyanate, and c) a fraction containing at least 95% by weight of bicyclic methylene diphenyl diisocyanate having a content of 4,4'-MDI of 49% by weight to 95.99% by weight, a content of 2,4'-MDI of 4% by weight to 45% by weight and a content of 2,2'-MDI of 0.01% by weight to 20% by weight, based on the mass of the fraction, is separated from the crude di- and polyisocyanate, and d) 4,4'-MDI is optionally removed from the fraction obtained in step c) to an extent of 10% to 98%, and e) 2,2'-MDI is wholly or partly removed from the fraction obtained in step c) or in step d) to obtain a fraction comprising 0% by weight to 0.4% by weight of 2,2'-MDI, 1% by weight to 95% by weight of 4,4'-MDI and 5% by weight to 98.6% by weight of 2,4'-MDI, based on the mass of the MDI isomers.

EP 1 686 112 A1 describes a process for preparing 2,4'-MMDI having a low level of 2,2'-MMDI by distilling a mixture of isomeric diisocyanato diphenylmethanes at least consisting of 2,2'-MMDI, 2,4'-MMDI and 4,4'-MMDI, using at least one dividing wall column. A mixture containing 85% by weight to 99% by weight of 2,4'-MMDI, a maximum of 15% by weight of 4,4'-MMDI and not more than 0.2% by weight of 2,2'-MMDI is obtained.

EP 1 792 895 A1 describes a process for preparing 4,4'-MMDI, in which a) aniline and formaldehyde in a molar ratio of 1.7 to 4:1 are converted in the presence of an acidic catalyst to di- and polyamines of the diphenylmethane series, and b) the di- and polyamines are reacted with phosgene to give the corresponding di- and polyisocyanates of the diphenylmethane series and optionally separated by distillation to obtain a mixture of di- and polyisocyanates of the diphenylmethane series (MDI) containing 44% by weight to 80% by weight of 4,4'-MMDI, and 1% by weight to 12% by weight of 2,4'- and/or 2,2'-MMDI in total, and 10% by weight to 55% by weight of PMDI, based on the weight of the MDI, and c) the MDI is separated into exactly two fractions by distillation and/or by crystallization, wherein the first fraction is obtained in amounts of 5% by weight to 40% by weight of the amount of MDI and the second fraction is obtained in amounts of 60% by weight to 95% by weight of the amount of MDI, and wherein the first fraction contains at least 97% by weight of 4,4'-MMDI and not more than 3% by weight of 2,4'-MMDI, based on the weight of the first fraction, and the second fraction contains 30% by weight to 60% by weight of 4,4'-MMDI, 1% by weight to 12% by weight of 2,4'-MMDI and not more than 2% by weight of 2,2'-MMDI, and 35% by weight to 65% by weight of PMDI, based on the weight of the second fraction.

Although it is not always mentioned explicitly, all processes for preparing isocyanates give secondary components having lower boiling points than the isocyanate to be prepared (called low boilers; e.g. phenyl isocyanate in the case of preparation of MDI) which have to be very substantially removed in the workup process. Low boilers are usually sent via an off-gas workup to incineration. The low boiler removal harbors the risk of entrainment of product of value. The state of the prior art does not address this, or at least does not do so sufficiently.

As an alternative to or especially also in conjunction with a distillative workup, crude isocyanates can also be worked up by crystallization (especially melt crystallization and/or suspension crystallization). This is described, for example, in WO2010/040675 A1 and WO2013/081873 A1. If an isocyanate fraction is obtained by crystallization, secondary components (such as the compounds having lower boiling points than the desired isocyanate that have been mentioned) generally remain in the uncrystallized phase.

SUMMARY

Irrespective of the exact mode of workup, there was therefore a need for further improvements in the workup of crude MDI, specifically of crude MMDI. More particularly, it would be desirable to separate secondary components, especially what are called the low boilers, from the desired target product with minimum loss of product of value, without impairing the economic viability of the process.

Taking this requirement into account, the present invention provides a process for obtaining methylene diphenylene diisocyanate and optionally a mixture of methylene diphenylene diisocyanate and polymethylene polyphenylene polyisocyanate, comprising the steps of:

α) providing a fraction comprising methylene diphenylene diisocyanate and secondary components with a proportion by mass of methylene diphenylene diisocyanate, based on its total mass and determined by gas chromatography, of more than 98.0% ("crude MMDI"; stream 142 in the drawings), optionally by α.1) separating methylene diphenylene diisocyanate and secondary components from a fraction ("crude MDI", stream 100 in the drawings) comprising methylene diphenylene diisocyanate and polymethylene polyphenylene polyisocyanate to obtain (i) a polymethylene polyphenylene polyisocyanate-enriched mixture of methylene diphenylene diisocyanate and polymethylene polyphenylene polyisocyanate ("MDI", stream 141 in the drawings) and (ii) the fraction comprising methylene diphenylene diisocyanate and secondary components with a proportion by mass of methylene diphenylene diisocyanate, based on its total mass and determined by gas chromatography, of more than 98.0% (142);

β) purifying, comprising an isomer separation, of the fraction (142) comprising methylene diphenylene diisocyanate and secondary components by distillation and/or crystallization in two or more, preferably in 3 to 10, more preferably in 4 to 8, partial steps (a, b, . . . ) to obtain at least (i) two or more, preferably two to four, more preferably two to three, pure methylene diphenylene diisocyanate fractions (140-1, 140-2, . . . ), each having a proportion by mass of methylene diphenylene diisocyanate, based on their total mass and determined by gas chromatography, of 99.9% or more and (ii) a secondary component fraction (150) having a proportion by mass, based on their total mass and determined by gas chromatography, of methylene diphenylene diisocyanate in the range from 20.0% to 98.0%, wherein the secondary component fraction (150) obtained in step β)

is returned to one of the partial steps (a, b, . . . ) of step β) in which none of the pure methylene diphenylene diisocyanate fractions (140-1, 140-2, . . . ) from step β) is obtained in the form of distillate or crystallizate, and/or, if conducted, to step α.1).

The "providing" of the crude MMDI in step α) can be effected either by preparing the crude MMDI in the same production site in which the purification in step β) is conducted or by preparing the crude MMDI elsewhere and transporting this crude MMDI to the production site at which the purification in step β) is conducted. In the latter case, the providing in step α) is effected simply by withdrawing the crude MMDI prepared elsewhere from a transport or storage tank or else from a long-distance pipeline.

A particularly appropriate process is, however, an integrated process for preparing and purifying MDI and MMDI in which step α) comprises the preparing of at least some, especially all, of the crude MMDI to be purified in step β). More particularly, therefore, the invention further provides a process for preparing methylene diphenylene diisocyanate (1a) and a mixture (1, MDI) of methylene diphenylene diisocyanate (1a) and polymethylene polyphenylene polyisocyanate (1b) from a mixture (2, MDA) of methylene diphenylene diamine (2a) and polymethylene polyphenylene polyamine (2b), comprising the steps of:

A)—part of step α)—reacting MDA (2) with phosgene (3) in the presence of an organic solvent (4), using phosgene (3) in a stoichiometric excess based on all the primary amino groups present, to obtain a liquid stream (60) comprising methylene diphenylene diisocyanate and polymethylene polyphenylene polyisocyanate and secondary components (and also organic solvent, dissolved hydrogen chloride and dissolved phosgene), and a gaseous stream (70) comprising hydrogen chloride and phosgene;

B) working up at least the liquid stream (60) comprising methylene diphenylene diisocyanate and polymethylene polyphenylene polyisocyanate and secondary components, comprising:

B.I)—part of step α)—a prepurification to remove a first portion of the secondary components to obtain a liquid fraction (100) depleted of secondary components (and of organic solvent, hydrogen chloride and phosgene) and comprising methylene diphenylene diisocyanate and polymethylene polyphenylene polyisocyanate;

B.II)—part of step α), corresponding to step α.1)—separating methylene diphenylene diisocyanate and a further portion of the secondary components from the fraction (100) depleted of secondary components and comprising methylene diphenylene diisocyanate and polymethylene polyphenylene polyisocyanate to obtain (i) a polymethylene polyphenylene polyisocyanate-enriched mixture (141 in the drawings, corresponding to 1) of methylene diphenylene diisocyanate and polymethylene polyphenylene polyisocyanate and (ii) a fraction (142) comprising methylene diphenylene diisocyanate and secondary components with a proportion by mass of methylene diphenylene diisocyanate, based on its total mass and determined by gas chromatography, of more than 98.0%;

B.III)—corresponding to step β)—purifying, comprising an isomer separation, of the fraction (142) comprising methylene diphenylene diisocyanate and secondary components by distillation and/or crystallization in two or more, preferably in 3 to 10, more preferably in 4 to 8, partial steps (a, b, . . . ) to obtain at least (i) two or more, preferably two to four, more preferably two to three, pure methylene diphenylene diisocyanate fractions (140-1, 140-2, . . . in the drawings; corresponding in each case to 1a), each having a proportion by mass of methylene diphenylene diisocyanate, based on their total mass and determined by gas chromatography, of 99.9% or more and (ii) a secondary component fraction (150) having a proportion by mass, based on their total mass and determined by gas chromatography, of methylene diphenylene diisocyanate in the range from 20.0% to 98.0%, wherein the secondary component fraction (150) obtained in step B.III)

is returned to one of the partial steps (a, b, . . . ) of step B.III) in which none of the pure methylene diphenylene diisocyanate fractions (140-1, 140-2, . . . ) from step B.III) is obtained in the form of distillate or crystallizate, and/or to step B.II)

(in this regard see also FIG. 1).

In this integrated process for preparing and purifying MDI and MMDI, steps A), B.I) and B.II) are part of step α), where step B.II) corresponds to step α.1). In addition, step B.III) corresponds to step β).

According to the invention, "secondary components" is understood to mean all constituents of product streams and fractions that do not correspond to any product of value to be prepared (MMDI, MDI) and are not organic solvent, hydrogen chloride or phosgene either. Examples of typical secondary components in this sense are phenyl isocyanate (PHI) and acridine hydrochloride (which sublimes very readily and hence can easily become part of distillate fractions). The secondary component fraction (150) obtained in step β) or step B.III) contains such secondary components in a proportion by mass of 2.0% to 80.0%, based on the total mass of the secondary component fraction (150). In view of the toxicity, for instance, of PHI (and in view of its monofunctionality), such fractions, even if the composition is at the lower end of the concentration range specified for the secondary components, are not usable as saleable products of value; they are therefore typically incinerated in the prior art.

A "partial step (a, b, . . . )" in step β) or step B.III) is understood here to mean a separation step in which a starting fraction (especially the fraction (142) containing methylene diphenylene diisocyanate and secondary components or an intermediate fraction obtained therefrom on the route to the end product—the pure methylene diphenylene diisocyanate fractions (140-1, 140-2, . . . )—is separated into two or more, especially into two or three, fractions. In the case of a distillative purification, a separation step especially comprises a distillation column familiar to the person skilled in the art (including peripheral equipment required, such as evaporators, condensers and the like). In the case of a purification by crystallization, a separation step especially comprises a crystallization reactor familiar to the person skilled in the art (also called "crystallizer").

In accordance with the terminology customary in the technical literature, a "distillate" in the context of the present inventions is a fraction obtained by partial evaporation of the liquid feed to a distillation. Distillates in this context are taken from a distillation column at the top or as a side draw. By contrast with the bottom stream from a distillation column, which should not be regarded as a distillate in the context of the present invention, distillates consist—possibly apart from entrained traces of unevaporated feed liquid—of constituents of the liquid feed that have been transferred to the gas phase. Distillates are initially obtained in gaseous form and are subsequently condensed. Such a condensation can firstly be undertaken in a "controlled" manner by supplying the distillate initially obtained in gaseous form to a condenser. A "controlled condensation" in this context may take place directly in the distillation column itself (for instance when a condenser is positioned in the distillation column in the region of or above the withdrawal point for the distillate) or in a condenser positioned outside the distillation column after withdrawal of the distillate in gaseous form. On the other hand, in a distillation column, depending on the exact configuration and mode of operation thereof, a liquid internal reflux that can be withdrawn in liquid form may arise from a distillate obtained in gaseous form even without contact with a condenser. A distillate can thus be withdrawn in liquid or gaseous form from a distillation column according to the configuration thereof and its mode of operation.

In accordance with the terminology customary in the specialist literature, a "crystallizate" in the context of the present inventions refers to a compound that has crystallized out of a liquid substance mixture, i.e. precipitated in solid form. The remaining liquid is referred to as mother liquor.

What follows first is a brief summary of different possible embodiments of the invention, wherein the enumeration of embodiments should be considered to be nonexhaustive:

In a first embodiment of the invention, which may be combined with all other embodiments, step α.1) is included.

In a second embodiment of the invention, which is a particular configuration of the first embodiment, the fraction (100) comprising methylene diphenylene diisocyanate and polymethylene polyphenylene polyisocyanate is obtained by the following steps:
A) reacting a mixture (2) of methylene diphenylene diamine and polymethylene polyphenylene polyamine with phosgene (3) in the presence of an organic solvent (4), using phosgene (3) in a stoichiometric excess based on all the primary amino groups present, to obtain a liquid stream (60) comprising methylene diphenylene diisocyanate and polymethylene polyphenylene polyisocyanate and secondary components, and a gaseous stream (70) comprising hydrogen chloride and phosgene;
B) working up at least the liquid stream (60) comprising methylene diphenylene diisocyanate and polymethylene polyphenylene polyisocyanate and secondary components, comprising:
a prepurification to remove a first portion of the secondary components to obtain the liquid fraction (100) depleted of secondary components and comprising methylene diphenylene diisocyanate and polymethylene polyphenylene polyisocyanate.

In a third embodiment of the invention, which is a particular configuration of the second embodiment, the organic solvent (4) used in step A) is selected from the group consisting of monochlorobenzene, dichlorobenzene, dioxane, toluene, xylene, methylene chloride, perchloroethylene, trichlorofluoromethane and butyl acetate.

In a fourth embodiment of the invention, which is a particular configuration of the second and third embodiments, the prepurification comprises the following steps:
(1) separating a gas stream (90) comprising hydrogen chloride and phosgene from the stream (60) comprising methylene diphenylene diisocyanate, polymethylene polyphenylene polyisocyanate and secondary components;
(2) separating a gas stream (110) comprising organic solvent (4) from the liquid phase remaining in step (1) after separation of the gas stream (90) comprising hydrogen chloride and phosgene to obtain the liquid fraction (100) depleted of secondary components and comprising methylene diphenylene diisocyanate and polymethylene polyphenylene polyisocyanate;
and optionally
(3) separating the gas stream (110) comprising organic solvent (4) into a liquid stream (120) comprising organic solvent (4) and a gas stream (130) comprising phosgene.

In a fifth embodiment of the invention, which is a particular configuration of the second to fourth embodiments, in step B), the gaseous stream (70) comprising hydrogen chloride and phosgene is also worked up, where this workup comprises:
separating phosgene from the gaseous stream (70) comprising hydrogen chloride and phosgene, especially after combining with the gas stream (90) comprising hydrogen chloride and phosgene, to obtain a gas stream (170) comprising hydrogen chloride, where, if present, the gas stream (130) comprising phosgene is also subjected to this phosgene separation step;
and optionally the additional step of
separating hydrogen chloride from the gas stream (170) comprising hydrogen chloride.

In a sixth embodiment of the invention, which is a particular configuration of the second to fifth embodiments, step β) is performed by distillation.

In a seventh embodiment of the invention, which is a particular configuration of the sixth embodiment, step β) comprises four to eight partial steps, wherein each partial step corresponds to a distillation in a distillation column without a dividing wall, wherein the first pure methylene diphenylene diisocyanate fraction (140-1) and the second pure methylene diphenylene diisocyanate fraction (140-2) are each obtained as distillate in different distillation columns, wherein the secondary component fraction (150) is obtained as distillate in a distillation column other than that for obtaining the first and second pure methylene diphenylene diisocyanate fraction, wherein a third pure methylene diphenylene diisocyanate fraction (140-3) is obtained as bottom product in this distillation column.

In an eighth embodiment of the invention, which is a particular configuration of the seventh embodiment, the secondary component fraction (150) is fed into the feed of the distillation column in which the secondary component fraction (150) has been obtained.

In a ninth embodiment of the invention, which is another particular configuration of the sixth embodiment, step β) comprises two or more partial steps, of which at least one partial step is conducted in a dividing wall column.

In a tenth embodiment of the invention, which is a particular configuration of the ninth embodiment, the stream (142) which comprises methylene diphenylene diisocyanate and secondary components and is obtained in step α.1) is transferred, in step β), into a dividing wall column from which two prepurified methylene diphenylene diisocyanate fractions (140-11, 140-22) are withdrawn as side streams in liquid form, and from which a top stream comprising secondary components and methylene diphenylene diisocyanate is withdrawn, wherein the prepurified methylene diphenylene diisocyanate fractions (140-11, 140-22, . . . ) are subjected to fine purification in further distillation stages to give a first and a second pure methylene diphenylene diisocyanate fraction (140-1, 140-2), wherein the top stream from the dividing wall column in a distillation column that comprises the secondary components and methylene diphenylene diisocyanate, which may optionally be configured as a side draw column with or without dividing wall, is distilled to obtain the secondary component fraction (150) as top stream, a third pure methylene diphenylene diisocyanate fraction (140-3) as bottom stream, and optionally a fourth pure methylene diphenylene diisocyanate fraction (140-4) as side stream, wherein the secondary component fraction (150) is recycled into step α.1) or into the dividing wall column from step β).

In an eleventh embodiment of the invention, which can be combined with all embodiments in which step β) is not conducted purely by distillation, step β) comprises at least one partial step in which a crystallization is performed, wherein the crystallizate obtained in the crystallization is a pure methylene diphenylene diisocyanate fraction or can be converted to a pure methylene diphenylene diisocyanate fraction by further purification.

In a twelfth embodiment of the invention, which is a particular configuration of the eleventh embodiment, the mother liquor obtained in the at least one partial step in which a crystallization is performed is distilled in at least two further partial steps, wherein at least one further pure methylene diphenylene diisocyanate fraction and the secondary component fraction (150) are obtained.

In a thirteenth embodiment of the invention, which is a particular configuration of the twelfth embodiment, the mother liquor is distilled in three further partial steps in which two pure methylene diphenylene diisocyanate fractions are obtained.

DETAILED DESCRIPTION

The embodiments briefly outlined above and further possible configurations of the invention are elucidated in more detail hereinafter. Various embodiments can be combined with one another as desired unless the opposite is clearly apparent to those skilled in the art from the context. The detailed outline is given on the basis of the integrated process for preparing and purifying MDI, but this should not be interpreted in a limiting manner.

Figure 1:
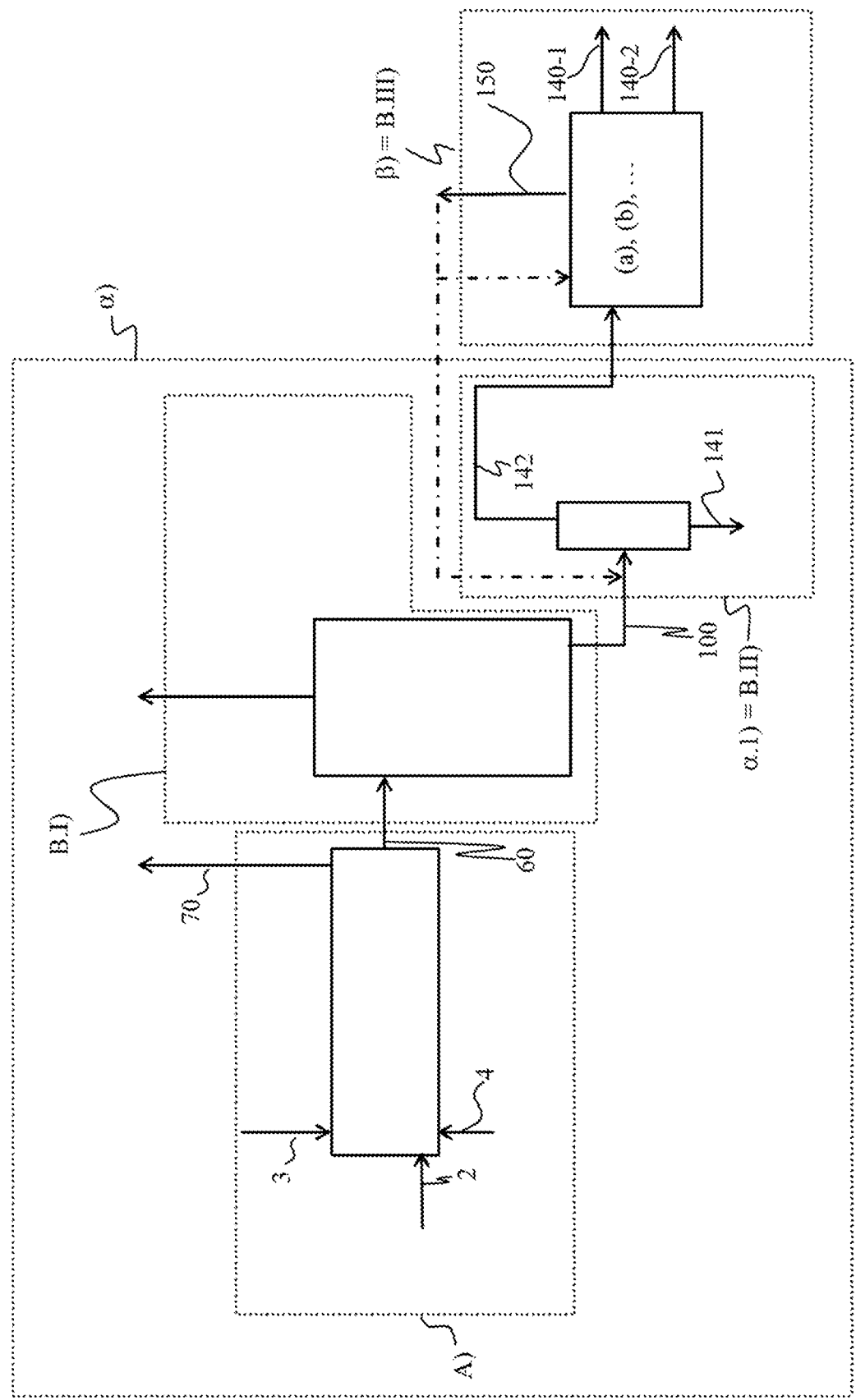
FIG. 1 shows the integrated process of the invention for preparing and purifying MDI in its broadest form purely schematically.

FIG. 1 shows the integrated process of the invention for preparing and purifying MDI in its broadest form purely schematically. The separation of organic solvent, hydrogen chloride, phosgene and a first portion of the secondary components in step B.I) is indicated schematically by the arrow leading upward. The inventive recycling of the secondary component fraction (150) into one of the partial steps (a, b, . . . ) of step B.III) in which none of the pure methylene diphenylene diisocyanate fractions (140-1, 140-2, . . . ) from step B.III is obtained and/or into step B.II) is represented by "dash-dot" arrows. In this case, the representation of the latter variant as feed into stream (100) should not be interpreted in a limiting manner; this recycling can of course also be effected by feeding the secondary component fraction (150) to step (B.II) separately from stream (100).

The continuous or semicontinuous, preferably continuous, production of MDI from MDA in step A) can be performed by one of the processes known from the prior art. Suitable processes are described, for example, in EP 2 077 150 A1, EP 1 616 857 A1, EP 1 873 142 A1, EP 0 716 079 A1 and EP 0 314 985 B1. Concentrations and flow rates of the amine (2) and phosgene (3) reactants are preferably chosen such that a molar ratio of phosgene to primary amino groups of 1.1:1 to 30:1, more preferably of 1.25:1 to 3:1, is established in the mixing of the co-reactants.

According to the invention, an organic solvent (4) is used in step A). Suitable organic solvents (4) usable in accordance with the invention are solvents that are inert under the reaction conditions, for example monochlorobenzene, dichlorobenzene (especially the ortho isomer), dioxane, toluene, xylene, methylene chloride, perchloroethylene, trichlorofluoromethane or butyl acetate. The inert solvent (4) is preferably essentially free of isocyanate (target proportion by mass <100 ppm) and essentially free of phosgene (target proportion by mass <100 ppm), and this should be noted when using recycled streams. Preference is therefore given to working by a process as described in EP 1 854 783 A2. The solvents can be used individually or in the form of any desired mixtures of the solvents mentioned by way of example. Preference is given to using monochlorobenzene (MCB) or ortho-dichlorobenzene (ODB). MCB is very particularly preferred.

In step B), at least the liquid stream (60) comprising methylene diphenylene diisocyanate and polymethylene polyphenylene polyisocyanate and secondary components is worked up.

The prepurification of the liquid stream (60) comprising methylene diphenylene diisocyanate and polymethylene polyphenylene polyisocyanate and secondary components (and also organic solvent, dissolved hydrogen chloride and dissolved phosgene) in step B.I) preferably comprises the following steps:

(1) separating a gas stream (90) comprising hydrogen chloride and phosgene from the stream (60) comprising methylene diphenylene diisocyanate, polymethylene polyphenylene polyisocyanate and secondary components (and also organic solvent, dissolved hydrogen chloride and dissolved phosgene);

(2) separating a gas stream (110) comprising organic solvent (4) from the liquid phase remaining in step (1) after separation of the gas stream (90) comprising hydrogen chloride and phosgene to obtain the liquid fraction (100) depleted of secondary components and comprising methylene diphenylene diisocyanate and polymethylene polyphenylene polyisocyanate;

and optionally (3) separating the gas stream (110) comprising organic solvent (4) into a liquid stream (120) comprising organic solvent (4) and a gas stream (130) comprising phosgene.

In this embodiment, the liquid stream (100) depleted of secondary components and comprising methylene diphenylene diisocyanate and polymethylene polyphenylene polyisocyanate is the liquid phase remaining after removal of the gas stream (110) containing organic solvent (4).

The separation of methylene diphenylene diisocyanate and a further portion of the secondary components from the fraction (100) depleted of secondary components and comprising methylene diphenylene diisocyanate and polymethylene polyphenylene polyisocyanate in step B.II) is effected by distillation, crystallization or a combination of the two, preferably by distillation.

The purification, comprising an isomer separation, of the fraction (142) comprising methylene diphenylene diisocyanate and secondary components in two or more partial steps (a, b, . . . ) in step B.III) is likewise effected by distillation, crystallization or a combination of the two, preferably by distillation.

Preferably, in step B), the gaseous stream (70) comprising hydrogen chloride and phosgene is also worked up, in which case this workup comprises the following:

B.IV) separating phosgene from the gaseous stream (70) comprising hydrogen chloride and phosgene, especially after combining with the gas stream (90) comprising hydrogen chloride and phosgene, to obtain a gas stream (170) comprising hydrogen chloride, where, if present, the gas stream (130) comprising phosgene is also subjected to this phosgene separation step;

and optionally

B.V) separating hydrogen chloride from the gas stream (170) comprising hydrogen chloride.

One possible configuration of the integrated process of the invention comprising steps A), B.I) (1), (2), (3), B.IV) and B.V) is elucidated hereinafter with reference to FIG. 2 (the recycling of the secondary component fraction (150) which is essential to the invention is not yet shown there for reasons of simplification of the drawing; in this regard, reference is made to the detailed drawings FIG. 3a-b discussed hereinafter).

MDA (2) and phosgene (3) are supplied in step A) from corresponding reservoir vessels (1020, 1030) to a suitable mixing zone (1100) and mixed therein. This is done in the form of solutions (20, 30) in the solvent (4). Suitable devices for the configuration of the mixing zone (1100) are sufficiently well known from the prior art. Mention is made by way of example of static mixing units (preferably nozzles) and dynamic mixing units (preferably rotor-stator mixers). After the mixing, the reaction mixture (50) is transferred into a reaction zone (1200). This is a residence time device in which the mixture obtained in the mixing zone (1100) is given sufficient opportunity to react to completion. Suitable apparatuses are sufficiently well known from the prior art (for example upright tubular reactors with upward flow, called "phosgenation towers"). The separation of the crude process product into the liquid phase (60) and gaseous stream (70) comprising hydrogen chloride and phosgene is effected in the actual reaction zone itself or in a separation zone (1210). It is also possible to integrate the mixing zone and reaction zone or the mixing zone, reaction zone and separation zone or the reaction zone and separation zone into a single apparatus (for example into a corresponding reactor). According to the invention, it is also possible for multiple mixing zones and/or reaction zones and/or, if present, separator zones to be connected in series or in parallel; for example in the form of a cascade of multiple series-connected reactors. The process product obtained in the reaction zone (1200) separates into a liquid phase (60) comprising, as well as MDI, also dissolved hydrogen chloride, excess dissolved phosgene, solvent and secondary components, and a gaseous stream (70) comprising hydrogen chloride gas, phosgene and gaseous solvent. The reaction zone may be followed, if required, by an apparatus for cleaving carbamoyl chloride (not shown in FIG. 2). In such a case, the liquid phase (60) passes through this apparatus before it is subjected to the workup in step B). The resultant hydrogen chloride-enriched gas phase is preferably combined with the gaseous stream (70) and they are subjected to further workup together.

The workup of the crude isocyanate in step B) firstly comprises, in step B.1), a depletion of phosgene and hydrogen chloride from the liquid phase (60) from step A) by separating this liquid stream (60) into a liquid stream (80) comprising solvent and isocyanate, and a gaseous gas stream (90) comprising phosgene and hydrogen chloride in a distillation apparatus (2100; "dephosgenation column"). This "dephosgenation column" can be operated by any method known from the prior art, preferably as described in EP 1 854 783 B1, especially in paragraphs [0018] and [0023].

The liquid stream (80) thus obtained is separated in a distillation apparatus (2200; "solvent column") into a gas stream (110) still containing solvent and a liquid stream (100) containing isocyanate. This can be effected by any method known from the prior art, preferably as described in EP 1 854 783 B1, especially in paragraphs [0024] to [0027]. The distillation apparatus (2200) may also comprise two or more columns (this option is not shown in FIG. 2 for reasons of simplification of the drawing).

The process off-gas stream (110), preferably after liquefaction in a condenser (2310), is separated in a distillation apparatus (2300; "solvent stripper") into a liquid stream (120) containing solvent and a phosgene-containing gas stream (130). This can be effected by any method known from the prior art, preferably as described in EP 1 854 783 B1, especially in paragraphs [0027] and [0028].

The phosgene-containing gas streams (70), (90) and (130) thus obtained are cleaned (i.e. freed of the majority of the phosgene) in an absorption apparatus (2500; "phosgene absorber") by absorption in solvent (4) to obtain a liquid stream (160) comprising solvent and phosgene and a gaseous process off-gas stream (170) comprising hydrogen chloride and solvent, wherein the gaseous phosgene-containing process off-gas streams (70) and (90) are preferably first combined and the combined phosgene-containing process off-gas stream from (70) and (90) and the phosgene-containing process off-gas stream (130) are each condensed and then introduced in liquid form into the absorption apparatus (2500) (step B.IV)). This cleaning can be effected by any process known from the prior art, preferably as described in EP 2 093 215 A1.

The phosgene-containing gas stream (170) obtained in this way contains the hydrogen chloride formed in the reaction and is therefore preferably sent to a hydrogen chloride removal in the removal unit (2600) (step B.V)). This depletion of the hydrogen chloride content is preferably effected by absorption of hydrogen chloride in water or dilute hydrochloric acid as absorbent (180) in a further absorption apparatus (2600; "HCl absorption column") to obtain a hydrochloric acid-containing stream (190) and, preferably after passing through a vapor condenser (2630) for very substantial removal of liquefiable constituents (191), a gaseous phosgene-containing process off-gas stream (200) comprising solvent and optionally gaseous secondary components. This step can be effected by any method known from the prior art. Preference is given to procedures as described in EP 1 743 882 B1, especially in paragraphs [0027] to [0038].

The absorbent (180) used is water (e.g. steam condensate) or hydrochloric acid in a concentration in the range from 0.50% by mass to 15.0% by mass (dilute hydrochloric acid). The heat released in the absorption of the hydrogen chloride transfers solvent present in stream (170) predominantly or completely to the gas stream (200).

The phosgene-containing process off-gas stream (200) obtained in this way is sent to a phosgene decomposition (apparatus 3000, C), preferably comprising two (or more) parallel-connected, alternately operated and regenerated phosgene decomposition units (3011 and 3012). Phosgene is decomposed here catalytically, preferably over activated carbon, using an aqueous stream, to obtain a gaseous stream optionally comprising solvent and optionally gaseous secondary components, and a liquid stream comprising hydrochloric acid. Preferably, the process off-gas and the aqueous stream are conducted through the activated carbon bed in co-current flow. The gaseous process off-gas stream (210) leaving the phosgene decomposition unit is then, optionally after passing through an adsorption apparatus for removal of the last solvent residues (not shown in FIG. 2), fed to an incineration unit (apparatus 6000, D)).

For purification of the crude MDI that has been largely freed of solvent, phosgene and hydrogen chloride (crude MDI 100), MMDI is first partly removed in the "polymer removal" (apparatus 2410) (step B.II)). This polymer removal can be effected by distillation, crystallization or a combination of the two, preferably by distillation. In each case, a fraction (142) is obtained, comprising, as well as MMDI, a further portion of the secondary components present in the liquid crude product (60) initially obtained (monomer fraction, called crude MMDI). Step B.II) is especially configured such that secondary components that are low-boiling or volatile relative to MMDI (for example PHI or remains of solvent that have not been fully removed in the preceding steps) are removed with this monomer fraction as far as possible, such that the remaining mixture of methylene diphenylene diisocyanate and polymethylene polyphenylene polyisocyanate (called polymer fraction, 141) already has the purity desired for further use. This is best achieved by a distillative separation. It is therefore preferable to separate the crude MDI (stream 100) in a distillation column (2410) into a distillate fraction (stream 142) comprising MMDI and secondary components, and a PMDI-enriched mixture of MMDI and PMDI (stream 141, bottom stream). Possible configurations for this purpose are known to the person skilled in the art and are described, for example, in EP 1 561 746 A2, especially in paragraph [0038] and in the examples, and in DE 3145010 A1, especially at page 7 lines 17 ff. and in FIG. 1.

According to the invention, the crude MMDI (142) thus removed contains more than 98.00% by mass of MMDI, based on the total mass thereof. The remaining MDI mixture (141) of MMDI and PMDI, as such or after addition of MMDI-containing streams obtained in step B.III), has various uses in polyurethane chemistry.

The monomer fraction (142) obtained in step B.II)—directly or after intermediate storage in a tank vessel which is optionally also fed with monomer fractions provided in some other way, comprising methylene diphenylene diisocyanate in a proportion by mass of more than 98.0%, based on its total mass and determined by gas chromatography, and secondary components—can be fed to step B.III).

The monomer fraction (142) is purified in step B.III) in two or more partial steps (a, b, . . . ) to obtain at least (i) two or more pure methylene diphenylene diisocyanate fractions (140-1, 140-2, . . . ), each having a proportion by mass of methylene diphenylene diisocyanate, based on their total mass and determined by gas chromatography, of 99.9% or more and (ii) a secondary component fraction (150) having a proportion by mass, based on their total mass and determined by gas chromatography, of methylene diphenylene diisocyanate in the range from 20.0% to 98.0%.

This purification in step B.III) can be effected by distillation, crystallization or a combination of the two, preferably by distillation. For reasons of simplification of the drawing, the overview drawing FIG. 2 shows this step merely in purely schematic form. Reference numeral 2400 and the assigned symbol here collectively represent a multitude of workup units. Possible configurations for the preferred distillative purification are shown hereinafter with reference to the more detailed figures FIG. 3a-b.

Figure 3A:
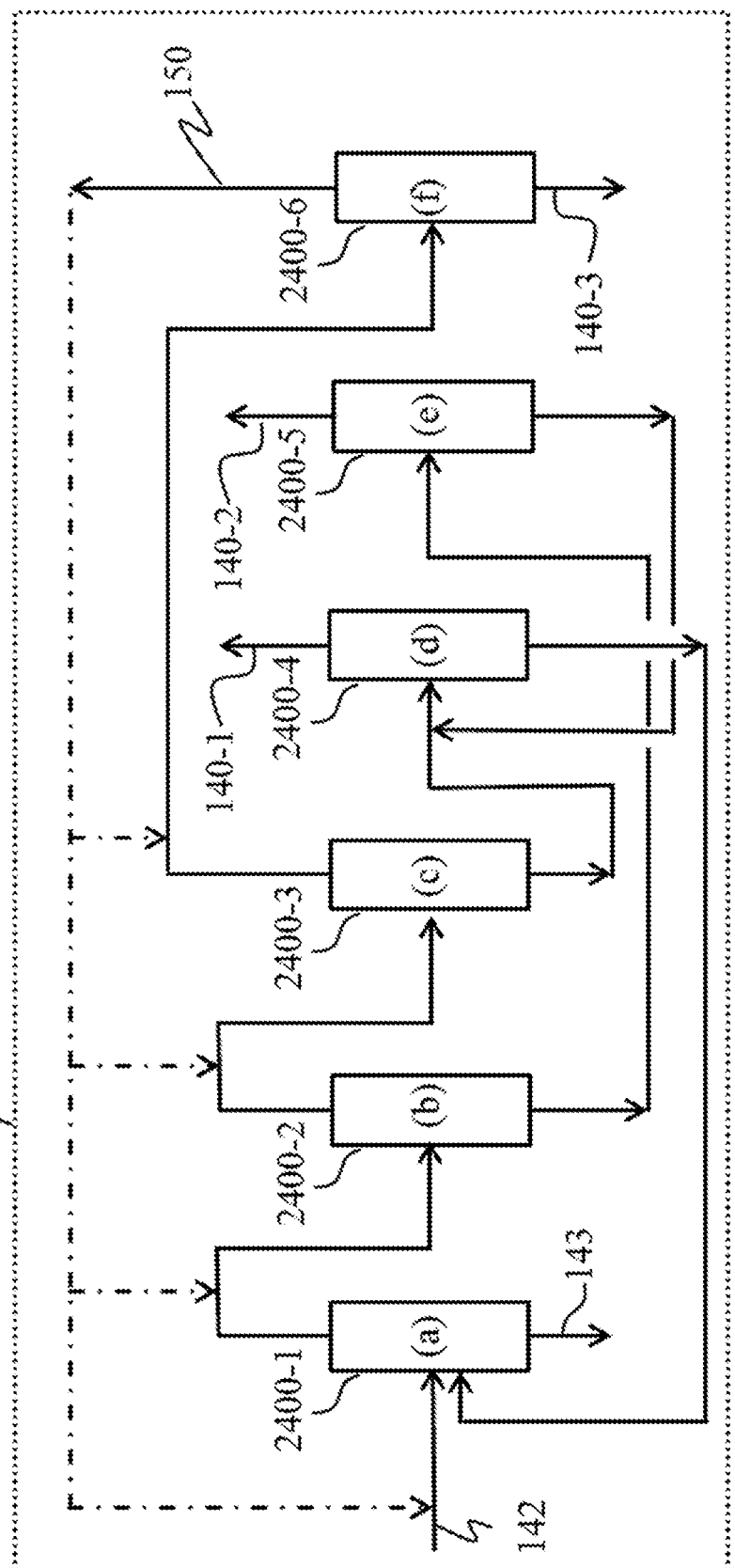
FIG. 3a shows a possible configuration of step B.III) of the process of the invention using six distillation columns (2400-1 to 2400-6) without a dividing wall.

FIG. 3a shows a possible configuration of step B.III) of the process of the invention using six distillation columns (2400-1 to 2400-6) without a dividing wall. Peripheral equipment, for example pumps, condensers and tanks, is omitted for reasons of simplification of the drawing. The individual distillates (obtained in gaseous form at first) are each condensed at a temperature in the range from 50° C. to 150° C. and a pressure in the range from 5 $mbar_{(abs.)}$ to 15 $mbar_{(abs.)}$. The chosen temperature depends on the composition of the isomer mixture of the respective distillate. Those constituents of the individual distillates that do not condense under the corresponding pressure and temperature conditions are removed into the vacuum system and ultimately into the off-gas system. Ultimately, in this way, the low boilers (components having a lower boiling point than 2,2'-MMDI) are withdrawn from the distillation system, but with much smaller losses of isocyanate compared to the prior art.

The stream (142) comprising MMDI and secondary components from step B.II) is transferred into a distillation column (2400-1) in a first partial step (a). In this distillation column, comparatively high-boiling secondary components and any entrained PMDI fractions are removed as bottom stream (143). This bottom stream additionally comprises monomer fractions, especially fractions of the highest-boiling isomer 4,4'-MMDI. The stream (143) has a proportion by mass of methylene diphenylene diisocyanate, based on its total mass and determined by gas chromatography, of less than 99.9% (namely especially from 50.0% to 99.5%) and can be blended, for example, with the MDI fractions (141) obtained in step B.II).

The distillate obtained in the first distillation column is then transferred into a further distillation column (2400-2) in a second partial step (b). The bottom product from this distillation column contains predominantly the highest-boiling isomer 4,4'-MMDI as well as small proportions of 2,4'-MMDI, while the distillate (top product) is a mixture of all isomers. To increase operational reliability, it may be advisable to maintain two parallel-connected, alternately operable distillation columns for this partial step (b) (not shown in FIG. 3a).

The distillate from the distillation column (2400-2) is then, in a third partial step (c), transferred into a further distillation column (2400-3) in which low-boiling secondary components are removed as distillate together with fractions of the MMDI isomers.

The bottom product from this third distillation column (2400-3), in a fourth partial step (d), is transferred into a further distillation column (2400-4) in which the first pure MMDI fraction (140-1) comprising predominantly the isomers 4,4'-MMDI and 2,4'-MMDI as well as minor proportions of 2,2'-MMDI is obtained as distillate. This pure MMDI fraction (140-1) contains preferably 0.0% by mass to 2.0% by mass of 2,2'-MMDI, 30.0% by mass to 70.0% by mass of 2,4-MMDI and 30.0% by mass to 70.0% by mass of 4,4'-MMDI, based on the total mass of all MMDI isomers.

The bottom product from the second distillation column (2400-2), in a fifth partial step (e), is transferred into a distillation column (2400-5). The second pure MMDI fraction (140-2), comprising predominantly the 4,4'-MMDI isomer, is obtained therein as distillate. It is also conceivable, rather than a single distillation column (2400-5), to use two series-connected distillation columns (2400-51, 2400-52), in which case the second pure MMDI fraction (140-2) is obtained as distillate from the second distillation column (2400-52) in flow direction (not shown in FIG. 3a). In this embodiment, the separations of matter conducted in each of distillation columns 2400-51 and 2400-52 should be regarded as separate partial steps in the context of the invention. In any case, the pure MMDI fraction (140-2) contains preferably 0.0% by mass to 1.0% by mass of 2,2'-MMDI, 0.1% by mass to 5.0% by mass of 2,4-MMDI and 94.0% by mass to 99.9% by mass of 4,4'-MMDI, based on the total mass of all MMDI isomers.

The bottom product from this fifth distillation column (2400-5) is fed together with the bottom product from the third distillation column (2400-3) to the fourth distillation column (2400-4).

The distillate from the third distillation column (2400-3), in a sixth partial step (f), is transferred into a further distillation column (2400-6, "low boiler column"). The secondary component fraction (150) is obtained as distillate therein, while a third pure MMDI fraction (140-3) containing all isomers is obtained as bottom product. This can either be used further as such or blended with other fractions, for example with MDI fractions (140) obtained in step B.II). This pure MMDI fraction (140-3) contains preferably 10.0% by mass to 60.0% by mass of 2,2'-MMDI, 30.0% by mass to 80.0% by mass of 2,4-MMDI and 0.0% by mass to 20.0% by mass of 4,4'-MMDI, based on the total mass of all MMDI isomers. The secondary component fraction (150) preferably has a proportion by mass of methylene diphenylene diisocyanate, based on its total mass, in the range from 20.0% to 98.0%, preferably 60% to 98%.

What is essential to the invention is that the secondary component fraction (150) is returned to a point in the workup at which none of the pure methylene diphenylene diisocyanate fractions (140-1, 140-2, . . . ) from step B.III) is obtained in the form of distillate. In this regard, FIG. 3a shows possible performance variants for this embodiment (represented by "dash-dot" arrows): The secondary component fraction (150) can—after substantial liquefaction; see above—be transferred into the feed to the first distillation column (2400-1) and/or into the feed to the second distillation column (2400-2) and/or into the feed to the third distillation column (2400-3) and/or into the feed to the sixth distillation column (2400-6). For energy-related reasons, preference is given to feeding solely into the feed to the sixth distillation column (2400-6).

It has been found that, entirely surprisingly, this procedure does not lead to an unacceptable accumulation of low boilers in the product of value streams, and the low boilers are instead discharged sufficiently via the off-gas system (and ultimately incinerated). The process of the invention thus allows partial to complete utilization of the MMDI components present in the secondary component fraction (150) (which can in any case account for up to 98.0% by mass of this stream) without any adverse effect on product quality.

In a departure from the embodiment of FIG. 3a, it is also possible to perform step B.III) using dividing wall columns and hence to reduce the number of distillation columns required. This is shown in an embodiment that needs only four distillation columns (2400-1 to 2400-4) in FIG. 3b. Peripheral equipment, for example pumps, condensers and tanks, is omitted for reasons of simplification of the drawing. The individual distillates that are obtained in gaseous form at first are each condensed, in the respective distillation column or in a condenser positioned outside, at a temperature in the range from 50° C. to 150° C. and a pressure in the range from 5 $mbar_{(abs.)}$ to 15 $mbar_{(abs.)}$. The chosen temperature depends on the composition of the isomer mixture of the respective distillate. Those constituents of the individual distillates that do not condense under the corresponding pressure and temperature conditions are removed into the vacuum system and ultimately into the off-gas system.

The stream (142) comprising MMDI and secondary components from step B.II) is transferred into a distillation column (2400-1) with a dividing wall (called a dividing wall column) in a first partial step (a). Two side streams are withdrawn in liquid form from this dividing wall column:

The upper side stream (140-11) contains a mixture of all isomers and, in a second partial step (b), is subjected to a fine purification in a second distillation column (2400-2)—without a dividing wall—to obtain the pure MMDI fraction (140-1) as distillate. The pure MMDI fraction (140-1) contains preferably 0.0% by mass to 2.0% by mass of 2,2'-MMDI, 30.0% by mass to 70.0% by mass of 2,4-MMDI and 30.0% by mass to 70.0% by mass of 4,4'-MMDI, based on the total mass of all MMDI isomers.

The lower side stream (140-22) contains predominantly the highest-boiling isomer 4,4'-MMDI as well as small proportions of 2,4'-MMDI, and, in a third partial step (c), is subjected to a fine purification in a third distillation column (2400-3)—without a dividing wall—to obtain the pure MMDI fraction (140-2) as distillate. The pure MMDI fraction (140-2) contains preferably 0.0% by mass to 1.0% by mass of 2,2'-MMDI, 0.1% by mass to 5.0% by mass of 2,4-MMDI and 94.0% by mass to 99.9% by mass of 4,4'-MMDI, based on the total mass of all MMDI isomers.

The bottom streams obtained in partial steps (b) and (c) are transferred into the feed to the dividing wall column.

The bottom stream (143) obtained in the dividing wall column contains comparatively high-boiling secondary components and any entrained PMDI fractions present. This bottom stream additionally comprises monomer fractions, especially fractions of the highest-boiling isomer 4,4'-MMDI. The stream (143) has a proportion by mass of methylene diphenylene diisocyanate, based on its total mass and determined by gas chromatography, of less than 99.9% (namely especially from 50.0% to 99.5%) and can be blended, for example, with the MDI fractions (141) obtained in step B.II).

The top stream obtained in the dividing wall column contains the low-boiling secondary components as well as fractions of MMDI. This stream, in a fourth partial step (d), is purified in a distillation column (2400-4) configured as a side draw column (without a dividing wall in FIG. 3b; but the use of a dividing wall column at this point is also possible) to free it of the secondary components, which are drawn off overhead as secondary component fraction (150), while the bottom product obtained is a third pure MMDI fraction (140-3) containing all isomers. This can either be used further as such or blended with other fractions, for example with MDI fractions (140) obtained in step B.II). This pure MMDI fraction (140-3) contains preferably 10.0% by mass to 60.0% by mass of 2,2'-MMDI, 30.0% by mass to 80.0% by mass of 2,4-MMDI and 0.0% by mass to 20.0% by mass of 4,4'-MMDI, based on the total mass of all MMDI isomers. The side draw stream (140-4) typically has an isomer distribution that is likewise within this range, but generally contains more secondary components. However, the demands on a pure MMDI fraction (not more than 0.1% secondary components) are met. In principle, it is also conceivable to operate the distillation column (2400-4) without a side draw; according to the mode of operation, in that case, the MMDI constituents and secondary components present in the side draw stream in the case of the execution according to FIG. 3b get into the secondary component fraction (150) drawn off overhead or into the bottom stream (140-3).

The secondary component fraction (150)—after very substantial liquefaction; see above—is transferred into the feed to the dividing wall column (2400-1) in this embodiment.

In all the embodiments outlined above, it is also possible to return the secondary component fraction (150) to step B.II) (polymer removal). For this purpose, the secondary component fraction (150)—after very substantial liquefaction; see above—can be transferred into the feed to the distillation column (2410).

The bottom stream (140-3) obtained in the embodiments outlined above, if required after blending with other pure MMDI fractions, can find use in many sectors. More particularly, mention should be made at this point of use in the production of sports floors, flexible foams and food packaging, and also use as wood binder.

Besides the embodiments outlined above with a purely distillative configuration of step B.III), this may also comprise crystallization steps. Examples of such embodiments can be found, for example, in EP1561746 A2 and documents cited therein, WO2010/095927 A1, and by M. Stepanski and P. Faessler in SULZER TECHNICAL REVIEW April 2002, pages 14 to 16.

Preference is given to combinations of crystallization and distillation steps. For example, in the embodiment according to FIG. 3a, the separation function of the second distillation column (2400-2) can be replaced by a crystallization step in which the highest-boiling 4,4'-MMDI isomer as well as small proportions of 2,4'-MMDI crystallizes out, while a mixture of all isomers remains as mother liquor. The mother liquor can subsequently be worked up by distillation in at least two further partial steps to obtain at least one pure methylene diphenylene diisocyanate fraction. This is preferably accomplished in three partial steps in distillation columns 2400-3, 2400-4 and 2400-6 in the manner described above to obtain two pure methylene diphenylene diisocyanate fractions (140-1 and 140-3). The crystallizate having a high 4,4'-MMDI content, for further purification to obtain the pure MMDI fraction (140-2), can be crystallized for a second time or—after liquefaction—distilled in distillation column 2400-5. However, this further purification is not absolutely necessary; if the crystallization that replaces the distillation in distillation column 2400-2 already affords the pure MMDI fraction (140-2) in sufficient purity, a further crystallization or distillation in distillation column 2400-5 is dispensable.

What is essential to the invention in this embodiment comprising crystallization steps too is that the secondary component fraction (150) is returned to a point in the workup at which none of the pure methylene diphenylene diisocyanate fractions (140-1, 140-2, . . . ) from step B.III) is obtained in the form of distillate or of crystallizate. This means that, when partial step (b) is replaced by such a crystallization that already affords the desired pure MMDI fraction (140-2) in sufficient purity such that further distillation or crystallization steps are dispensed with, the secondary component fraction (150) is not returned to partial step (b).

EXAMPLES

Methods of Analysis:

Viscosity: determination by means of falling ball viscometer or Brookfield viscometer (rotary viscometer).

NCO value: reaction with dibutylamine and back-titration of the unconverted dibutylamine with a standard HCl solution.

Composition: gas chromatography.

In examples 1 to 4, steps A) and B.I) were conducted as described in WO2017/050776 A1, page 35 line 2 to page 36 line 10 (although the amounts of MDA converted may be different). In example 5, corresponding conditions were used as the basis for a process simulation.

The crude MDI obtained as bottom product in this way, in examples 1 to 3, was subjected to a "polymer removal" according to step B.II) as follows (see also FIG. 2):

The crude MDI (corresponding to stream 100 in FIG. 2, with a flow rate of 5.4 t/h) was separated in a distillation column (2410) into a fraction containing MMDI and secondary components (the removal of secondary components such as phenyl isocyanate and solvent conducted in the preceding steps is not 100% successful) (crude MMDI; stream 142, 1.8 t/h), and a PMDI-enriched mixture of MMDI and PMDI (MDI; stream 141, 3.6 t/h). The distillation column (2410) was operated at a pressure of 8 mbar$_{(abs.)}$ and a bottom temperature of 220° C.

In example 4, step B.II) was conducted in a side draw column (without a dividing wall; feed 63 t/h) at a pressure of 10 mbar$_{(abs.)}$ and a bottom temperature of 225° C., withdrawing the crude MMDI (142) as sidestream. In example 5, corresponding conditions were used as the basis for a process simulation.

Figure 2:
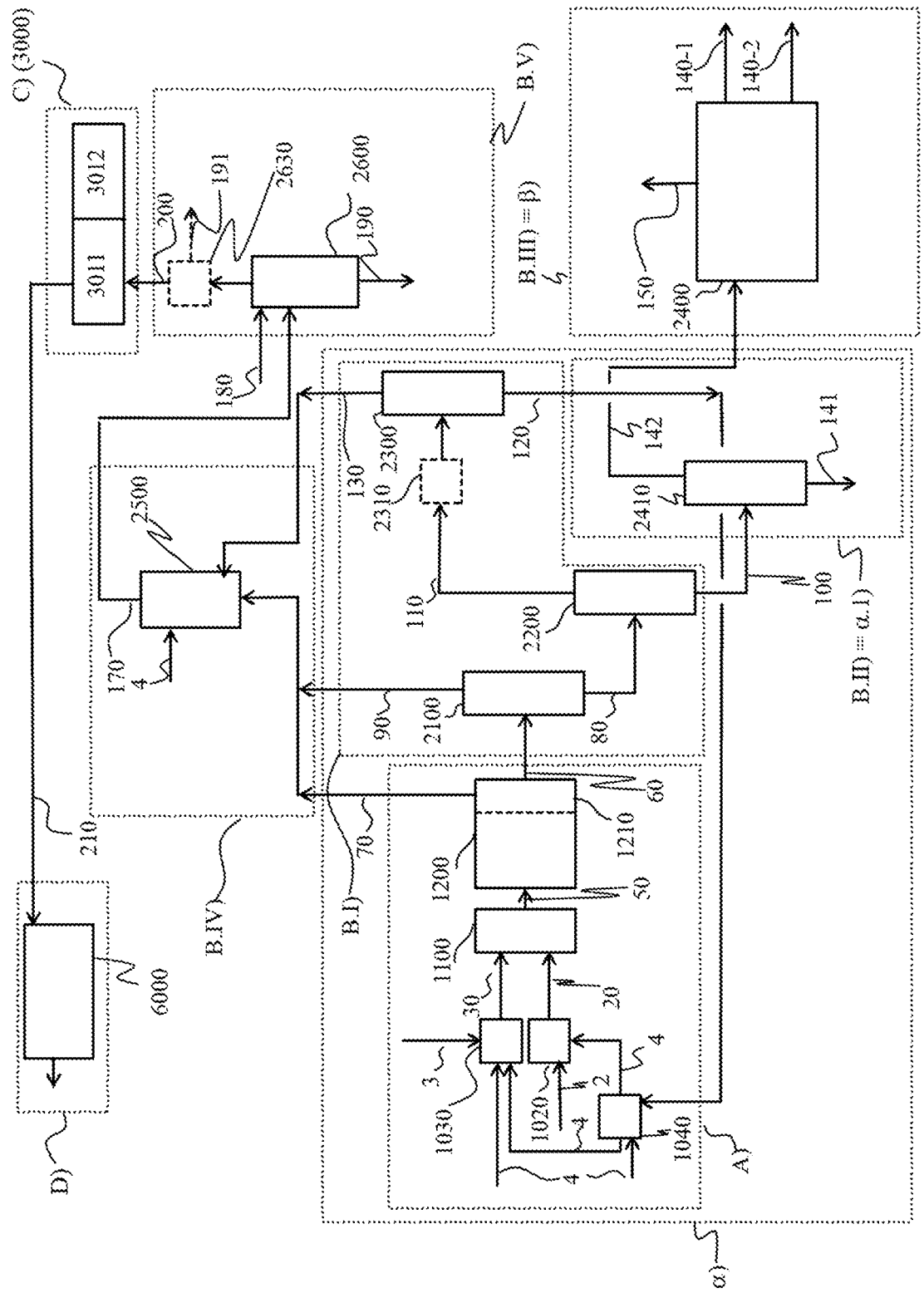
FIG. 2 shows one possible configuration of the integrated process of the invention comprising steps A), B.I)(1),(2),(3), B.IV) and B.V)

The fraction (142) containing MMDI and secondary components that has been obtained in this way in each of examples 1 to 4 was pumped into a storage tank (not shown in FIG. 2). The fraction (142) was withdrawn from this tank as starting material for the examples that follow.

Example 1 (Comparative Example—Distillation Columns without Dividing Wall)

Except for the recycling of the secondary component fraction (150), the purification and isomer separation were conducted by a process according to FIG. 3a (the secondary component fraction (150) was incinerated). The following operating parameters were observed here:

TABLE 1

Operating parameters in example 1

| Distillation column | Top pressure/ mbar$_{(abs.)}$ | Bottom temperature/ °C. | Top temperature/ °C. | Feed rate/ t h$^{-1}$ |
| --- | --- | --- | --- | --- |
| 2400-1 | 7.0 | 205 | 196 | 9.80 (fraction 142) |
|  |  |  |  | 1.00 (bottoms from 2400-4) |
| 2400-2 | 6.0 | 212 | 190 | 9.80 (distillate from 2400-1) |
| 2400-3 | 6.0 | 210 | 188 | 1.95 (distillate from 2400-2) |
| 2400-4 | 6.0 | 213 | 201 | 1.80 (bottoms from 2400-3) |
|  |  |  |  | 1.00 (bottoms from 2400-5) |
| 2400-5 | 6.0 | 210 | 197 | 7.85 (bottoms from 2400-2) |
| 2400-6 | 6.0 | 210 | 161 | 0.15 (distillate from 2400-3) |

The following streams left the distillation sequence:

TABLE 2

Product streams obtained in example 1

| Stream | Flow rate/ t h$^{-1}$ | Analysis | Note |
| --- | --- | --- | --- |
| 143 | 1.00 | 26.6% by mass of NCO Viscosity 217 mPa · s | Is mixed with stream 141 from B.II) or with other isocyanates. |
| 140-1 | 1.80 | 44.9% 4,4'-MMDI/ 55.0% 2,4'-MMDI/ 0.1% 2,2'-MMDI/ | Percent by mass based on total mass of MMDI, non-MMDI constituents present, if at all, in traces only (<10 ppm); saleable product. |
| 140-2 | 6.85 | 98.5% 4,4'-MMDI/ 1.5% 2,4'-MMDI | Percent by mass based on total mass of MMDI, non-MMDI constituents present, if at all, in traces only (<10 ppm); saleable product. |
| 140-3 | 0.10 | 6.3% 4,4'-MMDI/ 55.0% 2,4'-MMDI/ 38.7% 2,2'-MMDI/ | Percent by mass based on total mass of MMDI, non-MMDI constituents present, if at all, in traces only (<100 ppm); saleable product in principle; is generally fed into the feed to the polymer removal from B.II). |
| 150 | 0.050 | 97.5% MMDI/ 2.5% secondary components (PHI, MCB, etc.) | Is sent to incineration. |

Example 2 (Inventive—Distillation Columns without Dividing Wall)

The procedure was as in example 1, except that the secondary component fraction (150) was used as part of the feed to the distillation column 2400-1. The following operating parameters were observed here:

TABLE 3

Operating parameters in example 2

| Distillation column | Top pressure/ mbar$_{(abs.)}$ | Bottom temperature/ °C. | Top temperature/ °C. | Feed rate/ t h$^{-1}$ |
| --- | --- | --- | --- | --- |
| 2400-1 | 7.0 | 205 | 196 | 9.80 (fraction 142) |
|  |  |  |  | 1.00 (bottoms from 2400-45) |
|  |  |  |  | 0.035 (fraction 150) |
| 2400-2 | 6.0 | 212 | 190 | 9.84 (distillate from 2400-1) |
| 2400-3 | 6.0 | 210 | 188 | 1.99 (distillate from 2400-2) |
| 2400-4 | 6.0 | 213 | 201 | 1.80 (bottoms from 2400-3) |
|  |  |  |  | 1.00 (bottoms from 2400-5) |
| 2400-5 | 6.0 | 210 | 197 | 7.85 (bottoms from 2400-2) |
| 2400-6 | 6.0 | 210 | 161 | 0.15 (distillate from 2400-3) |
|  |  |  |  | 0.035 (fraction 150) |

The following streams left the distillation sequence:

TABLE 4

Product streams obtained in example 2

| Stream | Flow rate/ t h$^{-1}$ | Analysis | Note |
|---|---|---|---|
| 143 | 1.00 | 26.0% by mass of NCO Viscosity 298 mPa · s | Is mixed with stream 141 from B.II) or with other isocyanates. |
| 140-1 | 1.80 | 44.9% 4,4'-MMDI/ 55.0% 2,4'-MMDI/ 0.1% 2,2'-MMDI/ | Percent by mass based on total mass of MMDI, non-MMDI constituents present, if at all, in traces only (<10 ppm); saleable product. |
| 140-2 | 6.85 | 98.5% 4,4'-MMDI/ 1.5% 2,4'-MMDI | Percent by mass based on total mass of MMDI, non-MMDI constituents present, if at all, in traces only (<10 ppm); saleable product. |
| 140-3 | 0.14 | 65.1% 2,4'-MMDI/ 5.6% 4,4'-MMDI/ 29.3% 2,2'-MMDI/ | Percent by mass based on total mass of MMDI, non-MMDI constituents present, if at all, in traces only (<100 ppm); is obtained as a saleable product (can alternatively also be mixed, for example, with fraction 141 from B.II)). |

Example 3 (Inventive—Distillation Columns without Dividing Wall)

The procedure was as in example 1, except that the secondary component fraction (150) was used as part of the feed to the distillation column 2400-6. For this purpose, stream 150 was mixed with the distillate from distillation column 2400-3. The following operating parameters were observed here:

TABLE 5

Operating parameters in example 3

| Distillation column | Top pressure/ mbar$_{(abs.)}$ | Bottom temperature/ °C. | Top temperature/ °C. | Feed rate/ t h$^{-1}$ |
|---|---|---|---|---|
| 2400-1 | 7.0 | 205 | 196 | 9.80 (stream 142) 1.00 (bottoms from 2400-5) |
| 2400-2 | 6.0 | 212 | 190 | 9.80 (distillate from 2400-1) |
| 2400-3 | 6.0 | 210 | 188 | 1.95 (distillate from 2400-2) |
| 2400-4 | 6.0 | 213 | 201 | 1.80 (bottoms from 2400-3) 1.00 (bottoms from 2400-5) |
| 2400-5 | 6.0 | 210 | 197 | 7.85 (bottoms from 2400-2) |
| 2400-6 | 6.0 | 210 | 161 | 0.15 (distillate from 2400-3) 0.035 (stream 150) |

The following streams left the distillation sequence:

TABLE 6

Product streams obtained in example 3

| Stream | Flow rate/ t h$^{-1}$ | Analysis | Note |
|---|---|---|---|
| 143 | 1.00 | 25.6% by mass of NCO Viscosity 389 mPa · s | Is mixed with stream 141 from B.II). |
| 140-1 | 1.80 | 44.9% 4,4'-MMDI/ 55.0% 2,4'-MMDI/ 0.1% 2,2'-MMDI/ | Percent by mass based on total mass of MMDI, non-MMDI constituents present, if at all, in traces only (<10 ppm); saleable product. |
| 140-2 | 6.85 | 98.5% 4,4'-MMDI/ 1.5% 2,4'-MMDI | Percent by mass based on total mass of MMDI, non-MMDI constituents present, if at all, in traces only (<10 ppm); saleable product. |

TABLE 6-continued

Product streams obtained in example 3

| Stream | Flow rate/ t h$^{-1}$ | Analysis | Note |
|---|---|---|---|
| 140-3 | 0.14 | 7.1% 4,4'-MMDI/ 70.0% 2,4'-MMDI/ 22.9% 2,2'-MMDI/ | Percent by mass based on total mass of MMDI, non-MMDI constituents present, if at all, in traces only (<100 ppm); is obtained as a saleable product (can alternatively also be mixed, for example, with fraction 141 from B.II)). |

Examples 1 to 3 show that the inventive recycling of the secondary component fraction (150) enables an increase in the yield of the pure fraction 140-3 (because less isocyanates are transferred into the incineration with the secondary component fraction (150)), without any significant rise in the secondary component content in any product of value stream.

Example 4 (Comparative Example; Distillation Column with Dividing Wall)

Figure 3B:
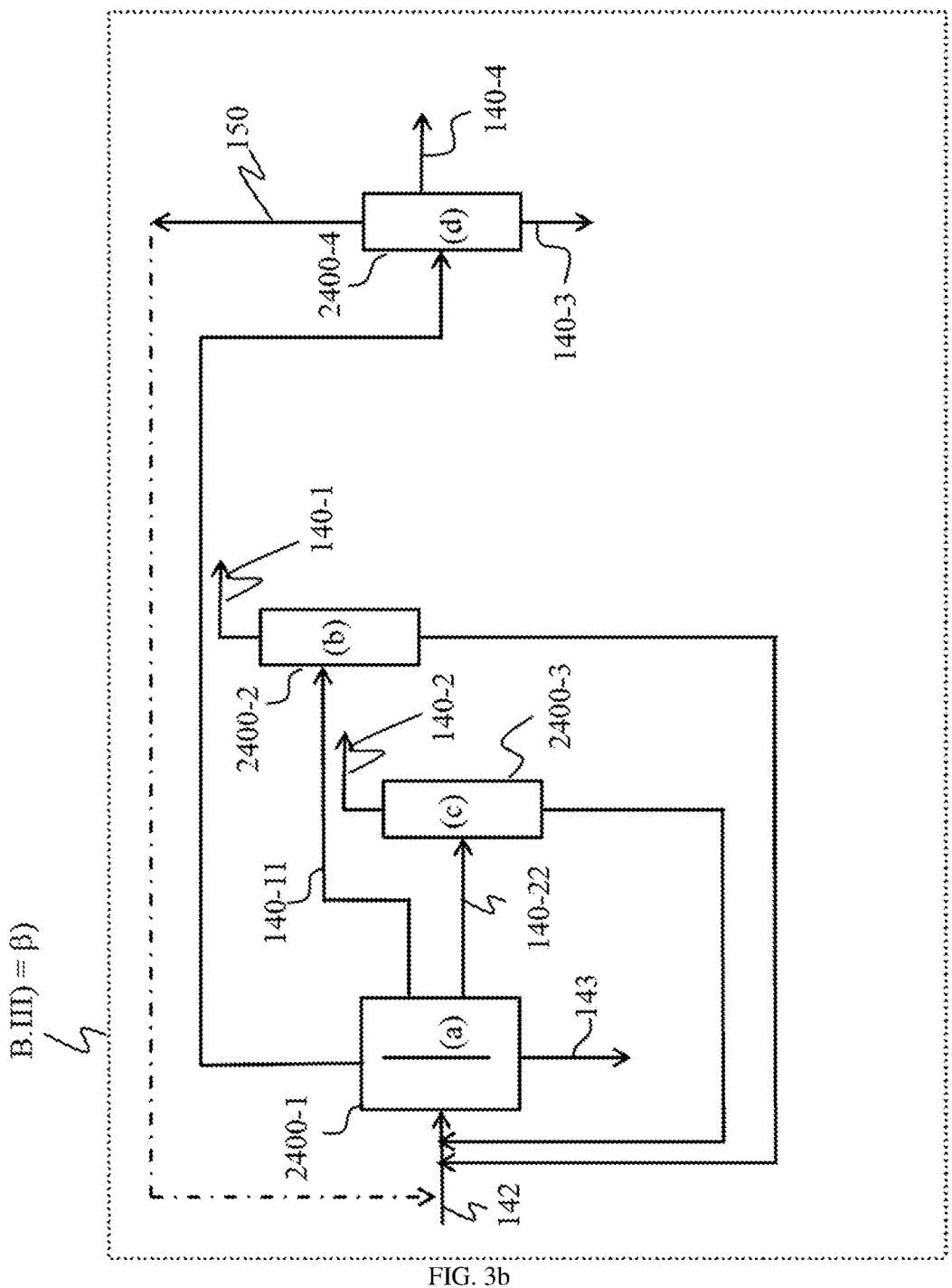
FIG. 3b shows a possible configuration of step B.III) of the process of the invention using a dividing wall column and four distillation columns (2400-1 to 2400-4).

The purification and isomer separation were conducted by a process according to FIG. 3b with the following exception:
The secondary component fraction (150) was not returned to the feed to the dividing wall column, but incinerated.
The following operating parameters were observed here:

TABLE 7

Operating parameters in example 4

| Distillation column | Top pressure/ mbar$_{(abs.)}$ | Bottom temperature/ ° C. | Top temperature/ ° C. | Feed rate/ t h$^{-1}$ |
|---|---|---|---|---|
| 2400-1 | 5.0 | 217 | 179 | 20.5 (stream 142) |
| 2400-2 | 5.0 | 189 | 174 | 3.3 (upper side stream from 2400-1; withdrawn there at 195° C.) |
| 2400-3 | 8.0 | 214 | 204 | 15.7 (lower side stream from 2400-1; withdrawn there at 200° C.) |
| 2400-4 | 10.0 | 215 | 195 | 1.6 (mixture of the top fractions drawn off in gaseous form from the dividing wall column (2400-1) and from the side draw column (2410) from step B.II) |

The following streams left the distillation sequence:

TABLE 8

Product streams obtained in example 4

| Stream | Flow rate/ t h$^{-1}$ | Analysis | Note |
|---|---|---|---|
| 143 | 1.0 | 26.1% by mass of NCOIs mixed with stream 141 from B.II). Viscosity 390 mPa · s | |
| 140-1 | 3.3 | 43.8% 4,4'-MMDI/ 56.1% 2,4'-MMDI/ 0.1% 2,2'-MMDI/ | Percent by mass based on total mass of MMDI, non-MMDI constituents present, if at all, in traces only (<10 ppm); saleable product. |
| 140-2 | 15.7 | 98.4% 4,4'-MMDI/ 1.6% 2,4'-MMDI | Percent by mass based on total mass of MMDI, non-MMDI constituents present, if at all, in traces only (<10 ppm); saleable product. |
| 140-3 | 0.80 | 13.6% 4,4'-MMDI/ 46.4% 2,4'-MMDI/ 40.0% 2,2'-MMDI | Percent by mass based on total mass of MMDI, non-MMDI constituents present, if at all, in traces only (<100 ppm); |

TABLE 8-continued

Product streams obtained in example 4

| Stream | Flow rate/ t h$^{-1}$ | Analysis | Note |
|---|---|---|---|
| Side draw from 2400-4 | 0.70 | 3.5% 4,4'-MMDI/ 57.5% 2,4'-MMDI/ 39.0% 2,2'-MMDI/ | saleable product in principle; is generally mixed, for example, with fraction 141 from B.II)). Percent by mass based on total mass of MMDI, non-MMDI constituents present, if at all, in traces only (<<0.1%); Use as ring fluid for the vacuum pumps; can alternatively also be blended with other pure MMDI fractions or used further as such. |
| 150 | 0.10 | 2.9% 2,4'-MMDI/ 92.1% 2,2'-MMDI/ 5.0% secondary components (PHI, MCB, acridine hydrochloride, etc.) | Is incinerated. |

Example 5 (Inventive—Distillation Column with Dividing Wall; Process Simulation)

The procedure is as shown in FIG. 3b (in other words, by contrast with example 4, the secondary component fraction (150) is not incinerated but recycled into the feed to the dividing wall column), but otherwise under the same operating conditions as in example 4. The yield of stream 140-3 is increased by 0.10 t/h to 0.90 t/h, with essentially the same composition of stream 140-3 (less isocyanates are transferred via the secondary component fraction (150) into the incineration, without any deterioration in product quality).

The invention claimed is:

1. A process for preparing methylene diphenylene diisocyanate and optionally a mixture of methylene diphenylene diisocyanate and polymethylene polyphenylene polyisocyanate, comprising:
   α) providing a fraction comprising methylene diphenylene diisocyanate and secondary components with a proportion by mass of methylene diphenylene diisocyanate, based on total mass of the fraction, of more than 98.0% when determined by gas chromatography, and
   β) purifying, comprising an isomer separation, the fraction comprising methylene diphenylene diisocyanate and secondary components by distillation and/or crystallization in two or more partial steps to obtain at least (i) two or more pure methylene diphenylene diisocyanate fractions, each having a proportion by mass of methylene diphenylene diisocyanate, based on their total mass, of 99.9% or more when determined by gas chromatography and (ii) a secondary component fraction having a proportion by mass, based on their total mass, of methylene diphenylene diisocyanate of 20.0% to 98.0% when determined by gas chromatography,
   wherein step α) optionally comprises:
   α.1) separating methylene diphenylene diisocyanate and secondary components from a fraction comprising methylene diphenylene diisocyanate and polymethylene polyphenylene polyisocyanate to obtain
      (i) a polymethylene polyphenylene polyisocyanate-enriched mixture of methylene diphenylene diisocyanate and polymethylene polyphenylene polyisocyanate and
      (ii) the fraction comprising methylene diphenylene diisocyanate and secondary components with a proportion by mass of methylene diphenylene diisocyanate, based on total mass of the fraction, of more than 98.0% when determined by gas chromatography;
   and
   wherein the secondary component fraction obtained in step β) is returned to:
   (1) one of the partial steps of step β) in which none of the pure methylene diphenylene diisocyanate fractions from step β) is obtained in the form of distillate or crystallizate,
   (2) step α.1), provided step α.1) is conducted, or
   (3) both:
      (a) one of the partial steps of step β) in which none of the pure methylene diphenylene diisocyanate fractions from step β) is obtained in the form of distillate or crystallizate, and
      (b) step α.1), provided step α.1) is conducted.

2. The process as claimed in claim 1, comprising step α.1).

3. The process as claimed in claim 2, in which the fraction comprising methylene diphenylene diisocyanate and polymethylene polyphenylene polyisocyanate is obtained by a process comprising:
   A) reacting a mixture of methylene diphenylene diamine and polymethylene polyphenylene polyamine with phosgene in the presence of an organic solvent, using phosgene in a stoichiometric excess based on all the primary amino groups present, to obtain a liquid stream comprising methylene diphenylene diisocyanate and polymethylene polyphenylene polyisocyanate and secondary components, and a gaseous stream comprising hydrogen chloride and phosgene;
   B) working up at least the liquid stream comprising methylene diphenylene diisocyanate and polymethylene polyphenylene polyisocyanate and secondary
   components, by a process comprising a prepurification to remove a first portion of the secondary components to obtain the fraction comprising methylene diphenylene diisocyanate and polymethylene polyphenylene polyisocyanate, which is depleted of secondary components.

4. The process as claimed in claim 3, in which the organic solvent used in step A) comprises monochlorobenzene, dichlorobenzene, dioxane, toluene, xylene, methylene chloride, perchloroethylene, trichlorofluoromethane or butyl acetate.

5. The process as claimed in claim 3, in which the prepurification comprises:
(1) separating a gas stream comprising hydrogen chloride and phosgene from the stream comprising methylene diphenylene diisocyanate, polymethylene polyphenylene polyisocyanate and secondary components;
(2) separating a gas stream comprising organic solvent from the liquid phase remaining in step 1) after separation of the gas stream comprising hydrogen chloride and phosgene to obtain the liquid fraction depleted of secondary components and comprising methylene diphenylene diisocyanate and polymethylene polyphenylene polyisocyanate; and optionally
(3) separating the gas stream comprising organic solvent into a liquid stream comprising organic solvent and a gas stream comprising phosgene.

6. The process as claimed in claim 3, in which, in step B), the gaseous stream comprising hydrogen chloride and phosgene is also worked up, where this workup comprises:
separating phosgene from the gaseous stream comprising hydrogen chloride and phosgene to obtain a gas stream comprising hydrogen chloride, where, if present, the gas stream comprising phosgene is also subjected to this phosgene separation step;
and optionally
separating hydrogen chloride from the gas stream comprising hydrogen chloride.

7. The process as claimed in claim 3, in which step β) is performed by distillation.

8. The process as claimed in claim 7, in which step β) comprises four to eight partial steps, wherein each partial step corresponds to a distillation in a distillation column without a dividing wall, wherein a first pure methylene diphenylene diisocyanate fraction and a second pure methylene diphenylene diisocyanate fraction are each obtained as distillate in different distillation columns, wherein the secondary component fraction is obtained as distillate in a distillation column other than that for obtaining the first and second pure methylene diphenylene diisocyanate fraction, wherein a third pure methylene diphenylene diisocyanate fraction is obtained as bottom product in the distillation column other than that for obtaining the first and second pure methylene diphenylene diisocyanate fraction.

9. The process as claimed in claim 8, in which the secondary component fraction is fed into the feed of the distillation column in which the secondary component fraction is obtained.

10. The process as claimed in claim 7, in which step β) comprises two or more partial steps, of which at least one partial step is performed in a dividing wall column.

11. The process as claimed in claim 10, in which the stream which comprises methylene diphenylene diisocyanate and secondary components and is obtained in step α.1) is transferred, in step β), into a dividing wall column from which two prepurified methylene diphenylene diisocyanate fractions are withdrawn as side streams in liquid form, and from which a top stream comprising secondary components and methylene diphenylene diisocyanate is withdrawn, wherein the prepurified methylene diphenylene diisocyanate fractions are subjected to fine purification in further distillation stages to give a first and a second pure methylene diphenylene diisocyanate fraction, wherein the top stream from the dividing wall column in a distillation column that comprises secondary components and methylene diphenylene diisocyanate, which may optionally be configured as a side draw column with or without dividing wall, is distilled to obtain the secondary component fraction as top stream, a third pure methylene diphenylene diisocyanate fraction as bottom stream, and optionally a fourth pure methylene diphenylene diisocyanate fraction as side stream, wherein the secondary component fraction is recycled into step α.1) or into the dividing wall column from step β).

12. The process as claimed in claim 1, in which step β) comprises at least one partial step in which a crystallization is performed, wherein the crystallizate obtained in the crystallization is a pure methylene diphenylene diisocyanate fraction or can be converted to a pure methylene diphenylene diisocyanate fraction by further purification.

13. The process as claimed in claim 12, in which a mother liquor obtained in the at least one partial step in which a crystallization is performed is distilled in at least two further partial steps, wherein at least one further pure methylene diphenylene diisocyanate fraction and the secondary component fraction are obtained.

14. The process as claimed in claim 13, in which the mother liquor is distilled in three further partial steps in which two pure methylene diphenylene diisocyanate fractions are obtained.

* * * * *